(12) United States Patent  (10) Patent No.: US 8,690,749 B1
Nunez  (45) Date of Patent: Apr. 8, 2014

(54) WIRELESS COMPRESSIBLE HEART PUMP

(76) Inventor: Anthony Nunez, Harrisburg, PA (US)

( * ) Notice: Subject to any disclaimer, the term of this patent is extended or adjusted under 35 U.S.C. 154(b) by 184 days.

(21) Appl. No.: 12/938,371

(22) Filed: Nov. 2, 2010

Related U.S. Application Data

(63) Continuation-in-part of application No. 12/846,820, filed on Jul. 29, 2010.

(60) Provisional application No. 61/257,173, filed on Nov. 2, 2009.

(51) Int. Cl.
*A61N 1/362* (2006.01)

(52) U.S. Cl.
USPC ............................................................ 600/16

(58) Field of Classification Search
USPC .................. 600/16–18; 623/3.1–3.3
See application file for complete search history.

(56) References Cited

U.S. PATENT DOCUMENTS

| | | |
|---|---|---|
| 1,071,042 A | 8/1913 | Fuller |
| 1,534,451 A | 4/1925 | Kauter |
| 1,711,045 A | 4/1929 | Davis |
| 1,739,000 A | 12/1929 | Jordao, Jr. |
| 1,759,766 A | 5/1930 | Szmukler |
| 1,926,444 A | 9/1933 | Jones |
| 1,972,780 A | 9/1934 | Laskowitz |
| 2,270,141 A | 1/1942 | Potter |
| 2,274,274 A | 2/1942 | Pezzillo |
| 2,470,794 A | 5/1949 | Snyder |
| 2,485,408 A | 10/1949 | Pezzillo |
| 2,500,400 A | 3/1950 | Cogswell |
| 2,535,695 A | 12/1950 | Pezzillo, Jr. |
| 2,537,310 A | 1/1951 | Lapp |
| 2,631,543 A | 3/1953 | Richmond |
| 2,652,505 A | 9/1953 | Matheisel |
| 2,697,986 A | 12/1954 | Meagher, Jr. |
| 2,711,286 A | 6/1955 | McAdam |
| 2,827,856 A | 3/1958 | Zozulin |
| 3,353,028 A | 11/1967 | Braikevitch et al. |
| 3,478,695 A | 11/1969 | Goranson at al |
| 3,479,960 A | 11/1969 | Cardoso |
| 3,487,784 A | 1/1970 | Rafferty et al. |
| 3,505,987 A | 4/1970 | Heilman |
| 3,708,251 A | 1/1973 | Pierro |

(Continued)

FOREIGN PATENT DOCUMENTS

| | | |
|---|---|---|
| CN | 1559626 A | 1/2005 |
| CN | 101361994 A | 2/2009 |

(Continued)

OTHER PUBLICATIONS

Qian et al, "World-first implantable aortic valvo-pump (IAVP) with sufficient haemodynamic capacity", Journal of Medical Engineering & Technology, Nov./Dec. 2005, pp. 302-304, vol. 29, No. 6, Taylor & Francis.

(Continued)

*Primary Examiner* — Christopher D Koharski
*Assistant Examiner* — Roland Dinga
(74) *Attorney, Agent, or Firm* — Albert W. Watkins

(57) ABSTRACT

An apparatus with a compressible construction having a wireless power source structured around a cylindrical-shaped support that suspends a motor within the vascular system while also supporting an impeller pump that can be made to be collapsible. The whole system allows for a minimally invasive pump implantation and augmentation of flow.

8 Claims, 20 Drawing Sheets

(56) References Cited

U.S. PATENT DOCUMENTS

| | | | |
|---|---|---|---|
| 3,719,436 A | 3/1973 | McFarlin |
| 3,791,769 A | 2/1974 | Kovacs |
| 4,123,666 A | 10/1978 | Miller |
| 4,135,253 A | 1/1979 | Reich et al. |
| 4,214,587 A | 7/1980 | Sakura |
| 4,375,941 A | 3/1983 | Child |
| 4,382,199 A | 5/1983 | Isaacson |
| 4,506,658 A | 3/1985 | Casile |
| 4,524,466 A | 6/1985 | Hall et al. |
| 4,625,712 A | 12/1986 | Wampler |
| 4,688,998 A | 8/1987 | Olsen et al. |
| 4,753,221 A | 6/1988 | Kensey et al. |
| 4,763,032 A | 8/1988 | Bramm et al. |
| 4,779,614 A | 10/1988 | Moise |
| 4,809,676 A | 3/1989 | Freeman |
| 4,817,586 A | 4/1989 | Wampler |
| 4,831,297 A | 5/1989 | Taylor et al. |
| 4,908,012 A | 3/1990 | Moise et al. |
| 4,919,647 A | 4/1990 | Nash |
| 4,944,722 A | 7/1990 | Carriker et al. |
| 4,944,748 A | 7/1990 | Bramm et al. |
| 4,949,022 A | 8/1990 | Lipman |
| 4,957,504 A | 9/1990 | Chardack |
| 4,962,734 A | 10/1990 | Jorgensen |
| 4,969,865 A | 11/1990 | Hwang et al. |
| 4,994,017 A | 2/1991 | Yozu |
| 5,017,103 A | 5/1991 | Dahl |
| 5,026,264 A | 6/1991 | Morozumi et al. |
| 5,040,944 A | 8/1991 | Cook |
| 5,049,134 A | 9/1991 | Golding et al. |
| 5,055,005 A | 10/1991 | Kletschka |
| 5,078,741 A | 1/1992 | Bramm et al. |
| 5,088,899 A | 2/1992 | Blecker et al. |
| 5,092,844 A | 3/1992 | Schwartz et al. |
| 5,112,200 A | 5/1992 | Isaacson et al. |
| 5,112,292 A | 5/1992 | Hwang et al. |
| 5,112,349 A | 5/1992 | Summers et al. |
| 5,147,281 A | 9/1992 | Thornton et al. |
| 5,183,222 A | 2/1993 | Ramsey, Jr. |
| 5,195,877 A | 3/1993 | Kletschka |
| 5,205,721 A | 4/1993 | Isaacson |
| 5,209,650 A | 5/1993 | Lemieux |
| 5,211,546 A | 5/1993 | Isaacson et al. |
| 5,234,447 A | 8/1993 | Kaster et al. |
| 5,257,151 A | 10/1993 | Cooper et al. |
| 5,290,227 A | 3/1994 | Pasque |
| 5,300,112 A | 4/1994 | Barr |
| 5,326,344 A | 7/1994 | Bramm et al. |
| 5,370,509 A | 12/1994 | Golding et al. |
| 5,376,114 A | 12/1994 | Jarvik |
| 5,399,074 A | 3/1995 | Nose et al. |
| 5,470,208 A | 11/1995 | Kletschka |
| 5,474,429 A | 12/1995 | Heidelberg et al. |
| 5,490,768 A | 2/1996 | Veronesi et al. |
| 5,494,413 A | 2/1996 | Campen et al. |
| 5,507,629 A | 4/1996 | Jarvik |
| 5,527,159 A | 6/1996 | Bozeman, Jr. et al. |
| 5,588,812 A | 12/1996 | Taylor et al. |
| 5,591,197 A | 1/1997 | Orth et al. |
| 5,613,935 A | 3/1997 | Jarvik |
| 5,627,421 A | 5/1997 | Miller et al. |
| 5,685,700 A | 11/1997 | Izraelev |
| 5,690,693 A | 11/1997 | Wang et al. |
| 5,695,471 A | 12/1997 | Wampler |
| 5,707,218 A | 1/1998 | Maher et al. |
| 5,713,939 A | 2/1998 | Nedungadi et al. |
| 5,729,066 A | 3/1998 | Soong et al. |
| 5,733,313 A | 3/1998 | Barreras, Sr. et al. |
| 5,735,897 A | 4/1998 | Buirge |
| 5,746,709 A | 5/1998 | Rom et al. |
| 5,749,855 A * | 5/1998 | Reitan ........................... 604/151 |
| 5,754,425 A | 5/1998 | Murakami |
| 5,755,748 A | 5/1998 | Borza |
| 5,769,877 A | 6/1998 | Barreras, Sr. |
| 5,792,157 A | 8/1998 | Mische et al. |
| 5,796,827 A | 8/1998 | Coppersmith et al. |
| 5,820,542 A | 10/1998 | Dobak, III et al. |
| 5,827,171 A | 10/1998 | Dobak, III et al. |
| 5,888,241 A | 3/1999 | Jarvik |
| 5,891,183 A | 4/1999 | Zierhofer |
| 5,922,019 A | 7/1999 | Hankh et al. |
| 5,924,848 A | 7/1999 | Izraelev |
| 5,928,280 A | 7/1999 | Hansen et al. |
| 5,945,762 A | 8/1999 | Chen et al. |
| 5,947,892 A | 9/1999 | Benkowski et al. |
| 5,948,006 A | 9/1999 | Mann |
| 5,951,263 A | 9/1999 | Taylor et al. |
| 5,957,672 A | 9/1999 | Aber |
| 6,000,915 A | 12/1999 | Hartman |
| 6,005,315 A | 12/1999 | Chapman |
| 6,015,272 A | 1/2000 | Antaki et al. |
| 6,020,665 A | 2/2000 | Maurio et al. |
| 6,042,347 A | 3/2000 | Scholl et al. |
| 6,050,975 A | 4/2000 | Poirier |
| 6,053,705 A | 4/2000 | Schob et al. |
| 6,058,593 A | 5/2000 | Siess |
| 6,068,588 A | 5/2000 | Goldowsky |
| 6,071,093 A | 6/2000 | Hart |
| 6,093,001 A | 7/2000 | Burgreen et al. |
| 6,100,618 A | 8/2000 | Schoeb et al. |
| 6,116,862 A | 9/2000 | Rau et al. |
| 6,135,729 A | 10/2000 | Aber |
| 6,136,025 A * | 10/2000 | Barbut et al. .................. 623/3.1 |
| 6,149,683 A | 11/2000 | Lancisi et al. |
| 6,176,822 B1 | 1/2001 | Nix et al. |
| 6,176,848 B1 | 1/2001 | Rau et al. |
| 6,186,665 B1 | 2/2001 | Maher et al. |
| 6,194,798 B1 | 2/2001 | Lopatinsky |
| 6,201,329 B1 | 3/2001 | Chen |
| 6,227,797 B1 | 5/2001 | Watterson et al. |
| 6,227,820 B1 | 5/2001 | Jarvik |
| 6,240,318 B1 | 5/2001 | Phillips |
| 6,244,835 B1 | 6/2001 | Antaki et al. |
| 6,254,359 B1 | 7/2001 | Aber |
| 6,293,901 B1 | 9/2001 | Prem |
| 6,327,504 B1 | 12/2001 | Dolgin et al. |
| 6,351,048 B1 | 2/2002 | Schob et al. |
| 6,447,265 B1 | 9/2002 | Antaki et al. |
| 6,447,266 B2 | 9/2002 | Antaki et al. |
| 6,474,341 B1 | 11/2002 | Hunter et al. |
| 6,482,228 B1 * | 11/2002 | Norred ........................ 623/2.17 |
| 6,527,521 B2 * | 3/2003 | Noda ........................... 417/355 |
| 6,533,716 B1 | 3/2003 | Schmitz-Rode et al. |
| 6,603,232 B2 | 8/2003 | Van Dine et al. |
| 6,616,421 B2 | 9/2003 | Mruk et al. |
| 6,626,644 B2 | 9/2003 | Ozaki |
| 6,644,125 B1 | 11/2003 | Siess et al. |
| 6,688,861 B2 | 2/2004 | Wampler |
| 6,716,157 B2 | 4/2004 | Goldowsky |
| 6,719,791 B1 | 4/2004 | Nusser et al. |
| 6,730,118 B2 | 5/2004 | Spenser et al. |
| 6,772,011 B2 | 8/2004 | Dolgin |
| 6,790,171 B1 | 9/2004 | Grundeman et al. |
| 6,794,789 B2 | 9/2004 | Siess et al. |
| 6,837,757 B2 | 1/2005 | Van Dine et al. |
| 6,981,942 B2 | 1/2006 | Khaw et al. |
| 6,989,027 B2 | 1/2006 | Allen et al. |
| 7,029,494 B2 | 4/2006 | Soun et al. |
| 7,070,398 B2 | 7/2006 | Olsen et al. |
| 7,144,364 B2 | 12/2006 | Barbut et al. |
| 7,147,661 B2 | 12/2006 | Chobotov et al. |
| 7,150,711 B2 | 12/2006 | Nusser et al. |
| 7,226,277 B2 | 6/2007 | Dooley |
| 7,229,258 B2 | 6/2007 | Wood et al. |
| 7,238,066 B2 | 7/2007 | Taylor et al. |
| 7,241,257 B1 | 7/2007 | Ainsworth et al. |
| 7,264,606 B2 | 9/2007 | Jarvik et al. |
| 7,338,530 B2 | 3/2008 | Carter et al. |
| 7,374,574 B2 | 5/2008 | Nuesser et al. |
| 7,393,181 B2 | 7/2008 | Mcbride et al. |
| 7,396,327 B2 | 7/2008 | Morello |
| 7,457,668 B2 | 11/2008 | Cancel et al. |
| 7,467,929 B2 | 12/2008 | Nusser et al. |
| 7,544,160 B2 | 6/2009 | Gross |

(56) References Cited

U.S. PATENT DOCUMENTS

| | | |
|---|---|---|
| 7,568,896 B2 | 8/2009 | Dooley |
| 7,648,454 B2 | 1/2010 | Sotiriou |
| 7,650,187 B2 * | 1/2010 | Gruber et al. .................. 607/33 |
| 7,699,586 B2 | 4/2010 | Larose et al. |
| 7,704,054 B2 | 4/2010 | Horvath et al. |
| 7,731,675 B2 | 6/2010 | Aboul-Hosn et al. |
| 7,736,296 B2 | 6/2010 | Siess et al. |
| 7,762,941 B2 | 7/2010 | Jarvik |
| 7,798,952 B2 | 9/2010 | Tansley et al. |
| 7,799,074 B2 | 9/2010 | Grimme et al. |
| 2002/0022759 A1 * | 2/2002 | Forsell ............................ 600/29 |
| 2003/0127090 A1 | 7/2003 | Gifford et al. |
| 2003/0212384 A1 | 11/2003 | Hayden |
| 2003/0233143 A1 * | 12/2003 | Gharib et al. .................. 623/3.1 |
| 2005/0049696 A1 | 3/2005 | Siess et al. |
| 2006/0008349 A1 | 1/2006 | Khaw |
| 2006/0036127 A1 * | 2/2006 | Delgado ......................... 600/16 |
| 2006/0195004 A1 | 8/2006 | Jarvik |
| 2006/0241745 A1 | 10/2006 | Solem |
| 2006/0259136 A1 | 11/2006 | Nguyen et al. |
| 2006/0271085 A1 | 11/2006 | Siess et al. |
| 2007/0004959 A1 | 1/2007 | Carrier et al. |
| 2007/0004986 A1 | 1/2007 | Korkala et al. |
| 2007/0005141 A1 | 1/2007 | Sherman |
| 2007/0078293 A1 | 4/2007 | Shambaugh, Jr. et al. |
| 2007/0142696 A1 | 6/2007 | Crosby et al. |
| 2007/0150009 A1 | 6/2007 | Kveen et al. |
| 2007/0225802 A1 | 9/2007 | Forsell |
| 2007/0299297 A1 | 12/2007 | Jarvik |
| 2008/0091265 A1 | 4/2008 | Nuesser et al. |
| 2008/0103591 A1 | 5/2008 | Siess |
| 2008/0114339 A1 | 5/2008 | McBride et al. |
| 2008/0132747 A1 | 6/2008 | Shifflette |
| 2008/0132748 A1 * | 6/2008 | Shifflette ......................... 600/16 |
| 2008/0140189 A1 | 6/2008 | Nguyen et al. |
| 2008/0195180 A1 | 8/2008 | Stevenson et al. |
| 2008/0215117 A1 | 9/2008 | Gross |
| 2008/0292478 A1 | 11/2008 | Baykut et al. |
| 2009/0005859 A1 | 1/2009 | Keilman |
| 2009/0043183 A1 | 2/2009 | Kermani et al. |
| 2009/0060743 A1 | 3/2009 | McBride et al. |
| 2009/0069854 A1 * | 3/2009 | Keidar et al. .................... 607/3 |
| 2009/0171448 A1 | 7/2009 | Eli |
| 2009/0204205 A1 | 8/2009 | LaRose et al. |
| 2010/0023093 A1 | 1/2010 | Govari et al. |
| 2010/0063347 A1 | 3/2010 | Yomtov et al. |
| 2010/0069847 A1 | 3/2010 | LaRose et al. |
| 2010/0076247 A1 | 3/2010 | Zilbershlag et al. |
| 2010/0094381 A1 | 4/2010 | Kim et al. |
| 2010/0125252 A1 | 5/2010 | Tseng et al. |
| 2010/0174131 A1 | 7/2010 | Foster et al. |

FOREIGN PATENT DOCUMENTS

| | | |
|---|---|---|
| CN | 101513545 A | 8/2009 |
| EP | 0764448 A2 | 9/1996 |
| EP | 0847767 A1 | 6/1998 |
| EP | 0914171 A2 | 5/1999 |
| FR | 2681384 A1 | 3/1993 |
| WO | WO 94/05347 A1 | 3/1994 |
| WO | WO 97/26703 A1 | 7/1997 |
| WO | WO 98/25657 A1 | 6/1998 |
| WO | WO 99/44651 A1 | 9/1999 |
| WO | WO 00/53239 A1 | 9/2000 |
| WO | WO 2006/051023 A1 | 5/2006 |
| WO | WO 2009/029959 A2 | 3/2009 |
| WO | WO 2009/046789 A1 | 4/2009 |
| WO | WO 2009/157840 A8 | 12/2009 |
| WO | WO 2010/119267 A1 | 10/2010 |
| WO | WO 2010/133567 A1 | 11/2010 |

OTHER PUBLICATIONS

Qian, "An Implantable Aortic Valvo-pump for Destination Therapy", Cardiovascular Engineering: An International Journal, Mar. 2006, pp. 41-43, vol. 6, No. 1, Springer Science+Business Media, Inc.

Chang et al, "A Global Sliding Mode Controller Design for an Intra-Aorta Pump", ASAIO Journal, 2010, pp. 510-516, American Society of Artificial Internal Organs.

Chang et al, "Modeling and Identification of an Intra-Aorta Pump", ASAIO Journal, 2010, pp. 504-509, American Society of Artificial Internal Organs.

Luukko, "Direct torque control of permanent magnet synchronous machines—analysis and implementation", Dissertation, 2000, pp. 1-184, Lappeenranta University of Technology, Finland.

Klempner et al, "Principles of Operation of Synchronous Machines", Operation and Maintenance of Large Turbo Generators, 2004, pp. 3-32, John Wiley & Sons, Inc.

"Motor Fundamentals", Rockwell Automation, Allen-Bradley, 7 pages.

Qiao et al, "A Simulation Study of Hemodynamic Benefits and Optimal Control of Axial Flow Pump-based Left Ventricular Assist Device", Biomechanical Systems Technology—Volume Set, 28 pages, World Scientific Publishing company Pte. Ltd.

Qian et al, "World-smallest LVAD with 27 g weight, 21mm OD and 5 1 min-1 flow with 50 mmHg pressure increase", Journal of Medical Engineering & Technology, May/Jun. 2007, pp. 181-184, vol. 31, No. 3, Informa UK Ltd.

* cited by examiner

WIRELESS COMPRESSIBLE HEART PUMP

CROSS REFERENCE TO RELATED APPLICATIONS

This application claims priority to U.S. provisional patent application Ser. No. 61/257,173 filed Nov. 2, 2009, entitled "Wirelessly Powered Left Ventricular Assist Device," and is a continuation in part of U.S. patent application Ser. No. 12/846,820 filed Jul. 29, 2010, entitled "Wireless Compressible Heart Pump," each naming the present inventor, the contents of each which are incorporated herein by reference in entirety.

BACKGROUND OF THE INVENTION

1. Field of the Invention

The present invention pertains generally to surgery, and more particularly to cardiac augmentation. In one preferred embodiment, a wirelessly powered, catheter delivered stent pump is capable of augmenting the circulation of fluid within the human body.

2. Description of the Related Art

Class IV heart failure carries a 50% mortality within two years of diagnosis. Displacement pumps were the initial pumps designed and built for implantation and support. The most successful was a pusher plate pump called the HeartMate I™. This device comprised of a pusher plate within a compliance chamber which displaced blood and provided pulsatile flow. These pumps were shown to be superior to optimal medical therapy in the Rematch Trial, but also demonstrated significant short and long term failure points including bleeding, infection, stroke, lung and renal failure surrounding the implantation procedure.

In recent years new cardiac assist devices operating as continuous flow devices have entered the clinical arena, the most successful of which has been an axial flow device called the HeartMate II™. This device has been proven successful in demonstrating the clinical feasibility of small axial flow devices in patients requiring a bridge to transplant or destination therapy. The continued drawbacks of these devices are the requirements for a surgical procedure for implantation, an external power source with limited battery life and significant morbidity and mortality associated with the implantation procedure and the aftercare.

Conventional axial flow devices such as the HeartMate II™ device often require a large operation because the patients are at the end of therapy and have already undergone most conventional procedures including stents for coronary artery disease, cardiopulmonary arterial bypass grafting, valve repair or replacement. Additionally, these patients may also already have undergone implantation of internal defibrillators to address issues of ventricular arrhythmias and ventricular dyschronicity associated with advanced degrees of heart failure.

The axial flow devices are based on the implantation of a rigid pump encased within an electromagnetic housing connected to an external power source which can be supplied by alternating current or direct current from a battery source. This pump, although efficient in design has ongoing issues with gastrointestinal bleeding, stroke, infection and pump thrombosis.

In addition to the foregoing commercial devices, there exists a very large body of patents form many artisans, each which have attempted to address the many issues and complications associated with a cardiac assist device. The following United States patents are exemplary of the art, the contents of each which is incorporated herein by reference for the teachings found therein: U.S. Pat. No. 3,505,987 by Heilman; U.S. Pat. No. 4,135,253 by Reich et al; U.S. Pat. No. 4,375,941 by Child; U.S. Pat. No. 4,524,466 by Hall et al; U.S. Pat. No. 4,625,712 by Wampler; U.S. Pat. No. 4,688,998 by Olsen et al; U.S. Pat. No. 4,753,221 by Kensey et al; U.S. Pat. No. 4,919,647 by Nash; U.S. Pat. No. 4,944,722 by Carriker et al; U.S. Pat. No. 4,994,017 by Yozu; U.S. Pat. No. 5,017,103 by Dahl; U.S. Pat. No. 5,040,944 by Cook; U.S. Pat. No. 5,257,151 by Cooper et al; U.S. Pat. No. 5,290,227 by Pasque; U.S. Pat. No. 5,370,509 by Golding et al; U.S. Pat. No. 5,376,114 by Jarvik; U.S. Pat. No. 5,399,074 by Nos+E et al; U.S. Pat. No. 5,507,629 by Jarvik; U.S. Pat. No. 5,527,159 by Bozeman, Jr. et al; U.S. Pat. No. 5,613,935 by Jarvik; U.S. Pat. No. 5,627,421 by Miller et al; U.S. Pat. No. 5,690,693 by Wang et al; U.S. Pat. No. 5,695,471 by Wampler; U.S. Pat. No. 5,713,939 by Nedungadi et al; U.S. Pat. No. 5,729,066 by Soong et al; U.S. Pat. No. 5,733,313 by Barreras, Sr. et al; U.S. Pat. No. 5,749,855 by Reitan; U.S. Pat. No. 5,754,425 by Murakami; U.S. Pat. No. 5,755,748 by Borza; U.S. Pat. No. 5,769,877 by Barreras, Sr.; U.S. Pat. No. 5,792,157 by Mische et al; U.S. Pat. No. 5,796,827 by Coppersmith et al; U.S. Pat. No. 5,888,241 by Jarvik; U.S. Pat. No. 5,891,183 by Zierhofer; U.S. Pat. No. 5,924,848 by Izraelev; U.S. Pat. No. 5,945,762 by Chen et al; U.S. Pat. No. 5,947,892 by Benkowski et al; U.S. Pat. No. 5,948,006 by Mann; U.S. Pat. No. 6,005,315 by Chapman; U.S. Pat. No. 6,015,272 by Antaki et al; U.S. Pat. No. 6,020,665 by Maurio et al; U.S. Pat. No. 6,042,347 by Scholl et al; U.S. Pat. No. 6,050,975 by Poirier; U.S. Pat. No. 6,071,093 by Hart; U.S. Pat. No. 6,116,862 by Rau et al; U.S. Pat. No. 6,136,025 by Barbut et al; U.S. Pat. No. 6,149,683 by Lancisi et al; U.S. Pat. No. 6,176,822 by Nix et al; U.S. Pat. No. 6,176,848 by Rau et al; U.S. Pat. No. 6,201,329 by Chen; U.S. Pat. No. 6,227,797 by Watterson et al; U.S. Pat. No. 6,227,820 by Jarvik; U.S. Pat. No. 6,240,318 by Phillips; U.S. Pat. No. 6,244,835 by Antaki et al; U.S. Pat. No. 6,293,901 by Prem; U.S. Pat. No. 6,327,504 by Dolgin et al; U.S. Pat. No. 6,351,048 by Schob et al; U.S. Pat. No. 6,474,341 by Hunter et al; U.S. Pat. No. 6,482,228 by Norred; U.S. Pat. No. 6,527,521 by Noda; U.S. Pat. No. 6,533,716 by Schmitz-Rode et al; U.S. Pat. No. 6,603,232 by Van Dine et al; U.S. Pat. No. 6,626,644 by Ozaki; U.S. Pat. No. 6,644,125 by Siess et al; U.S. Pat. No. 6,688,861 by Wampler; U.S. Pat. No. 6,716,157 by Goldowsky; U.S. Pat. No. 6,719,791 by Nusser et al; U.S. Pat. No. 6,730,118 by Spenser et al; U.S. Pat. No. 6,772,011 by Dolgin; U.S. Pat. No. 6,790,171 by Grundeman et al; U.S. Pat. No. 6,794,789 by Siess et al; U.S. Pat. No. 6,837,757 by Van Dine et al; U.S. Pat. No. 6,981,942 by Khaw et al; U.S. Pat. No. 6,989,027 by Allen et al; U.S. Pat. No. 7,070,398 by Olsen et al; U.S. Pat. No. 7,144,364 by Barbut et al; U.S. Pat. No. 7,229,258 by Wood et al; U.S. Pat. No. 7,238,066 by Taylor et al; U.S. Pat. No. 7,393,181 by Mcbride et al; U.S. Pat. No. 7,396,327 by Morello; U.S. Pat. No. 7,457,668 by Cancel et al; U.S. Pat. No. 7,544,160 by Gross; and U.S. Pat. No. 7,648,454 by Sotiriou.

Additional United States published patent applications for which the contents are incorporated herein by reference include: 2003\0127090; 2003\0212384; 2003\0233143; 2005\0049696; 2006\0008349; 2006\0036127; 2006\0195004; 2006\0241745; 2006\0259136; 2006\0271085; 2007\0004986; 2007\0005141; 2007\0142696; 2007\0150009; 2007\0225802; 2007\0299297; 2008\0103591; 2008\0114339; 2008\0132747; 2008\0132748; 2008\0140189; 2008\0140189; 2008\0195180; 2008\0215117; 2009\0005859; 2009\0043183; 2009\0060743;

2009\0069854; 2009\0171448; 2010\0023093; 2010\0063347; 2010\0076247; 2010\0094381; and 20100125252.

PCT published applications for which the contents are incorporated herein by reference include: WO2006\051023A1; WO2009\029959A2; WO9405347A1; and WO9944651A1.

In addition, Webster's New Universal Unabridged Dictionary, Second Edition copyright 1983, is incorporated herein by reference in entirety for the definitions of words and terms used herein.

SUMMARY OF THE INVENTION

In a first manifestation, the invention is a cardiac augmentation pump having a compressible construction and a wireless power source structured around a cylindrical-shaped support that suspends a motor within the vascular system while also supporting an impeller pump that can be made to be collapsible, the pump which allows for a minimally invasive pump implantation and augmentation of cardiac flow. The pump has an impeller pump support; struts and vanes; a main stent body; electromagnetic elements placed onto the main stent body; a wireless energy coil; a fluid impeller having impeller blades; a central hub on which the impeller blades are movably coupled; a motor; and a motor control. Other manifestations are contemplated herein as well.

OBJECTS OF THE INVENTION

Exemplary embodiments of the present invention solve inadequacies of the prior art by providing a ventricular assist pump for use in assisting cardiac function of the heart. The pump is collapsible for delivery and placement within the heart, and, upon delivery, expandable to a functional geometry. Wireless power and control enable either external or internal control of the pump.

BRIEF DESCRIPTION OF THE DRAWINGS

The foregoing and other objects, advantages, and novel features of the present invention can be understood and appreciated by reference to the following detailed description of the invention, taken in conjunction with the accompanying drawings, in which:

FIG. 14 illustrates a woven medical textile fabric with insulated wire coils woven in.

DESCRIPTION OF THE PREFERRED EMBODIMENT

Figure 1:
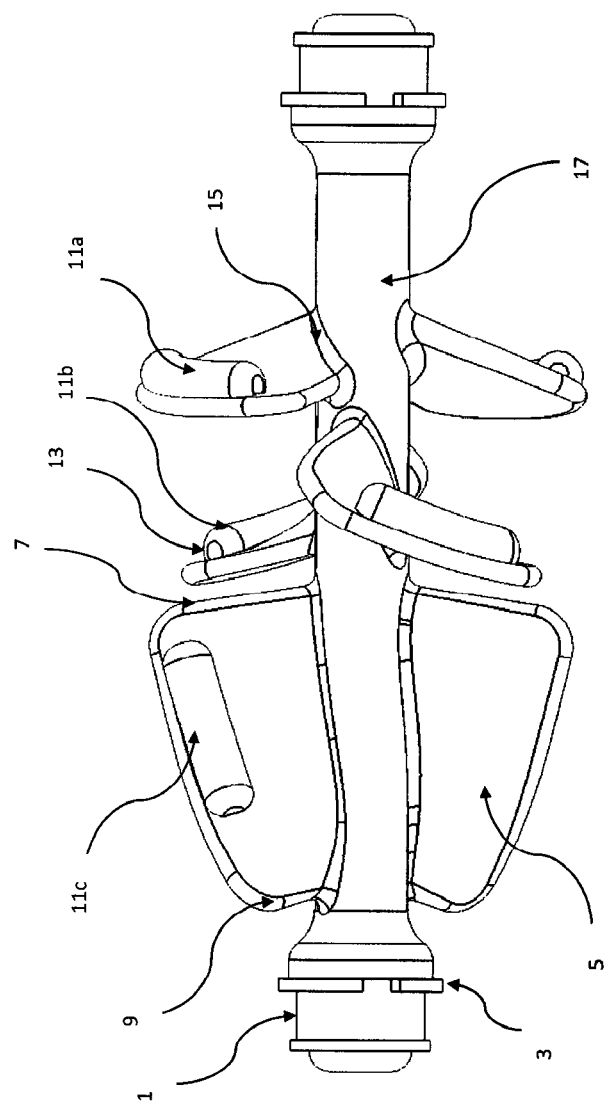
FIG. 1 illustrates the expanded impeller with the bearing element and the bearing lip movably coupled with the central rotating element.

FIG. 1 Illustrates the expanded impeller with the bearing element 1 and the bearing lip 3 movably coupled with the central rotating element 17. The central rotating element is substantially configured from deformable materials such as polymers, metal alloys or carbon based elements and may be constructed by coupling modular components which allow for the change in length as the network of wires comprising the pump change in length with expansion from the constrained state to the expanded state. The impeller blades 5 are formatted in several rows which are clocked and interleaved to allow for a mixed pump configuration. The mixed axial and centrifugal configuration is defined by adjusting the shrouding elements on the inner stent as well as the leading edge 7 angle, trailing edge 9 angle, chord angle and chord length of each blade. When in the constrained configuration the impeller blades are movable coupled around the central rotating element 17 and may utilize the magnetic interaction of the magnets in the impeller blade edges in 11a, 11b and 11c to either attract or repel and thus assist in constraining or expanding the blades. The magnetic are positioned by inserting through the magnet insertion opening 13. The magnet insertion opening may be round as the blade deforms in the preparation stage to allow the insertion of the magnet and once the magnet is inserted it configures to an asymmetric shape to prevent the migration of the magnet with rotation of the blade.

Figure 2:
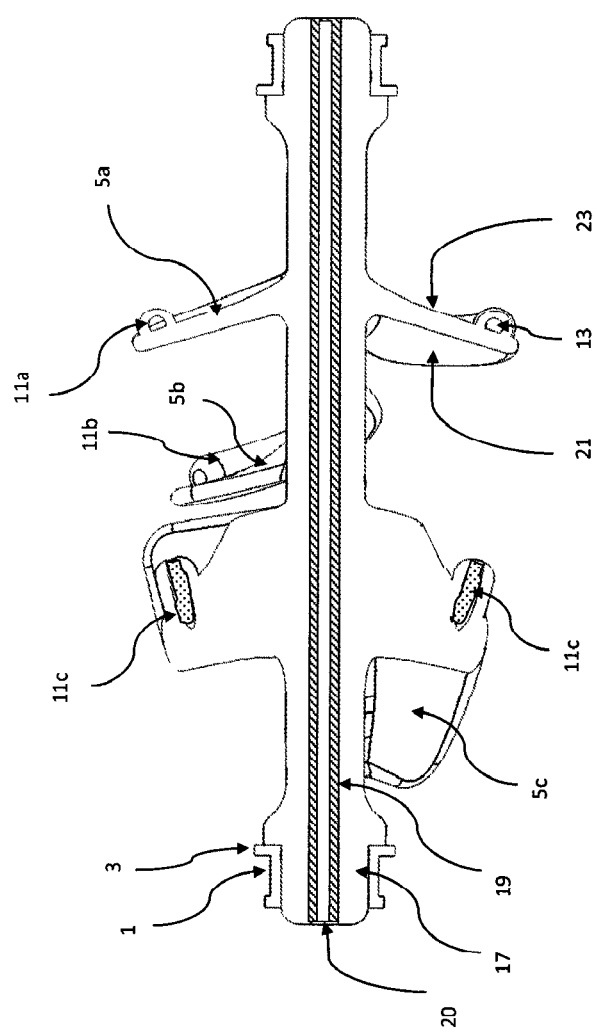
FIG. 2 illustrates the cross-section of the impeller blades with the embedded magnets detailed in the third row of impeller blades.

FIG. 2 illustrates the cross-section of the impeller blades 5a, 5b and 5c with the embedded magnets 11c detailed in the third row of impeller blades 5c. Two other rows of blades are drawn illustrating the plurality of blades that can be used to create an optimal pump configuration. The blades are in the expanded configuration and are drawn as being single entity that includes the central rotating element 17 movably coupled to the bearing system 1. Supporting the central rotating element 17 is a central rotating element support shaft 19 is hollowed out to form a guidewire slot 20. The guidewire slot 20 and support shaft 19 are movably coupled to the central rotating element 17 and the impeller blades 5a, 5b and 5c. As exemplified, The impeller blade 5a when expanded form a suction face 21 and a pressure face 23 with the magnet on the impeller blade edge 11a movably coupled to the edge via the magnet insertion point 13.

Figure 3:
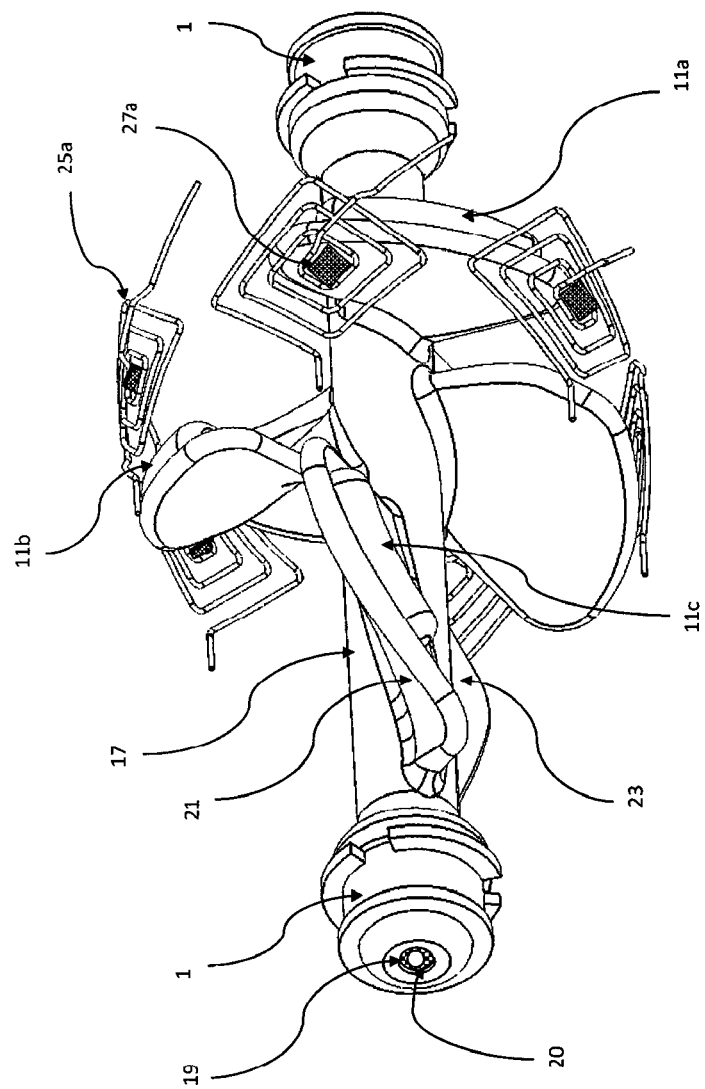
FIG. 3 illustrates an oblique view of the expandable impeller pump in the configuration of an expandable motor substantially composed of a row of stator coil elements with associated ferromagnetic elements, closely approximated to the first row of impeller magnets.

FIG. 3 is an oblique view of the expandable impeller pump in the configuration of an expandable motor substantially composed of a row of stator coil elements 25a with associated ferromagnetic elements 27a, closely approximated to the first row of impeller magnets 11a. A plurality of magnets embedded on the blade edges 11a, 11b and 11c are electromagnetically coupled to outer rows of stator elements. The bearing element 1 is movably coupled to the central rotating element supported by the central support shaft 19 being hollowed out to form a guidewire passage 20. The impeller pump once expanded and rotating, forms a suction face 21 and pressure face 23 with mixed axial and centrifugal flow characteristics generated from the rotational torque derived from the electromagnetic interaction of the expandable motor elements. The electromagnetic field forces created by the passage of an alternating current within the stator coil element 25a coupled to the magnets within the blade edges 11a also generates a back electromagnetic force current which can be used to sense and modify the rotational speed by varying the alternating current.

Figure 4:
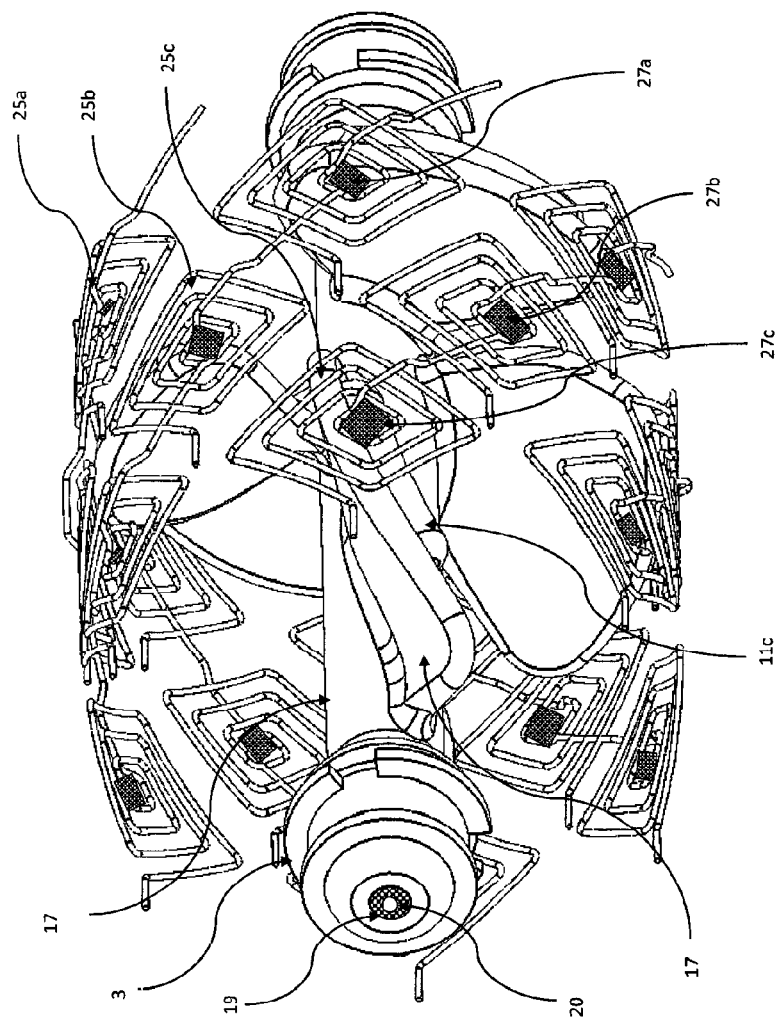
FIG. 4 illustrates an oblique view of the expanded motor and impeller with a plurality of impeller blades with magnet on the edges exemplified by 11c closely approximated to several rows of stator coils which contain several ferromagnetic elements.

FIG. 4 is an oblique view of the expanded motor and impeller with a plurality of impeller blades with magnet on the edges exemplified by 11c closely approximated to several rows of stator coils 25a, 25b and 25c which contain several ferromagnetic elements 27a, 27b and 27c. The impeller blades are clocked and interleaved to allow for a folding pattern around the central rotating element 17 that compresses the impeller to a diameter that allows for minimally invasive delivery either through a peripheral artery such as the femoral artery or subclavian artery or through the left ventricular apex directly into the ascending aorta. The central rotating element support shaft 19 and hollow guidewire passage 20 allow for a central guidewire to be used to guide the device in its compressed form to the ascending aorta and adjust its position across the aortic valve such that once activated the coronaries are still perfused and sufficient pressure is generated to maintain and augment perfusion to the distal organ beds. Additionally, the device can be placed in the venous system to augment right ventricular function or assist in decompressing the venous system.

Figure 5:
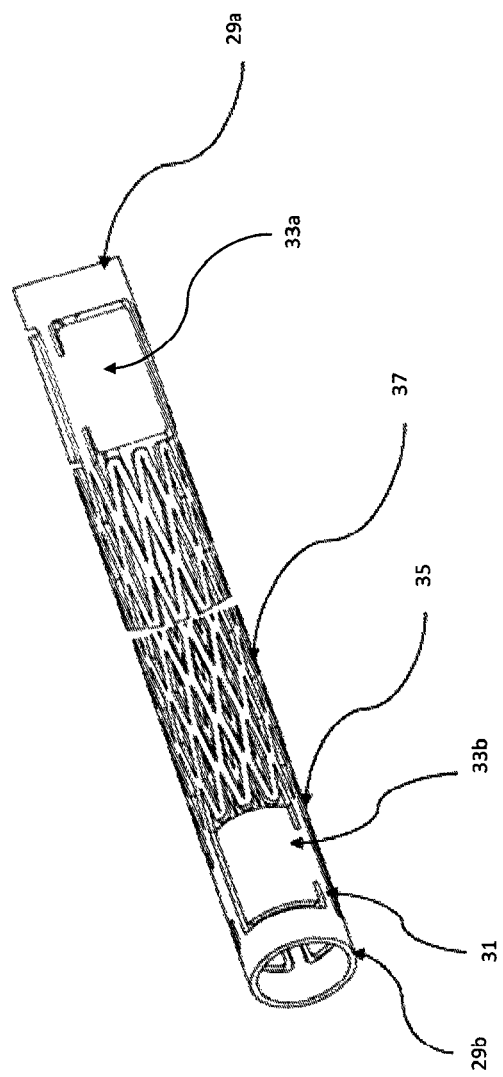
FIG. 5 illustrates the Inner Stent main body suspending the Impeller at the cylindrical support elements with one row of stator coils and ferromagnetic elements.

FIG. 5 illustrates the Inner Stent main body 37 suspending the Impeller at the cylindrical support elements 29 with one row of stator coils 25a and ferromagnetic elements 27a. The suspension of the components of a compressible pump requires a superstructure with an integrated motor that is self-expanding and will restore to a predictable configuration while allowing for full expansion of the impeller pump suspended within. A cylindrical-shaped impeller pump support structure is described in FIG. 5 by the presence of proximal 29a and distal 29b cylindrical support elements. The proximal and distal support elements are two smaller cylindrical-shaped non-compressible elements that are movably coupled to the main body of the inner stent 37 by proximal vane struts 31 and distal vane struts 35 that are varied in dimensions, preferably in diameter and height to accommodate the requirements of the pump. The proximal 29a and distal 29b cylindrical-shaped support elements of FIG. 5 are attached and movably coupled to the central stent by struts that are fashioned by laser cutting one single tube of material.

Figure 6:
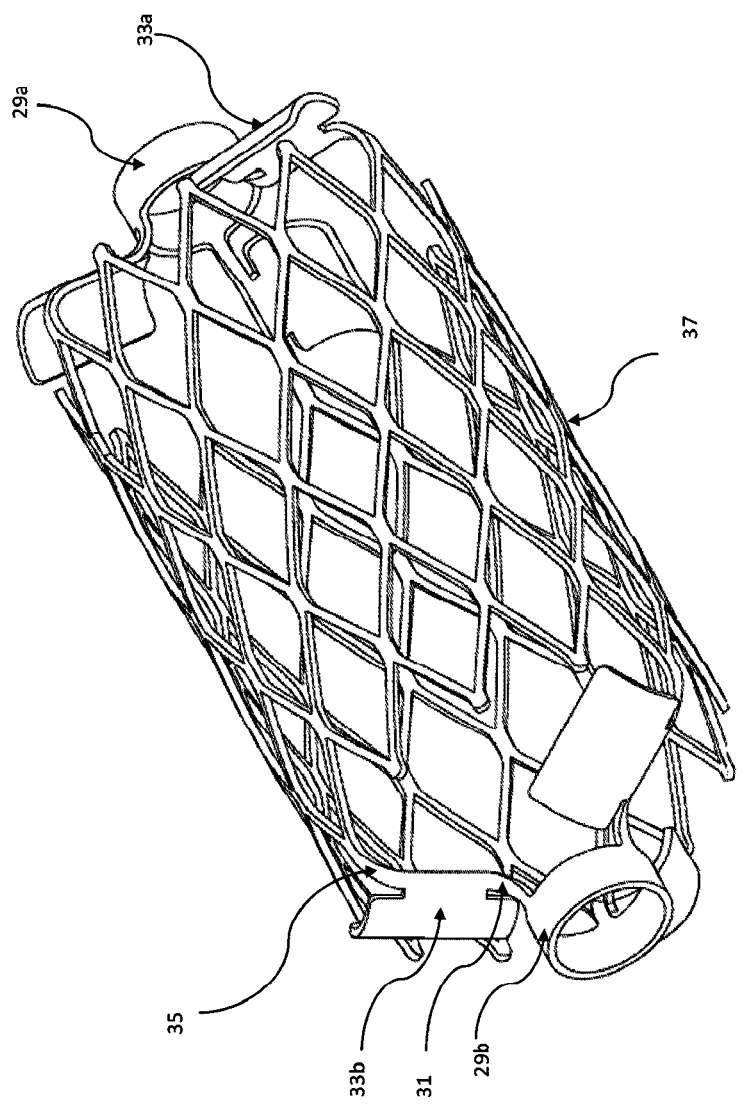
FIG. 6 illustrates an expanded embodiment of the inner main stent body with the cylindrical support elements, expanded proximal vane struts, and distal vane strut, movably coupled to the expanded but unfolded proximal vane elements and unfolded distal vane elements.

FIG. 6 demonstrates an expanded embodiment of the inner main stent body with the cylindrical support elements 29a and 29b, expanded proximal vane struts 31, and distal vane strut 35, movably coupled to the expanded but unfolded proximal vane elements 33a and unfolded distal vane elements 33b. The unfolded vane elements 33a and 33b are movably coupled to the main body of the inner stent 37.

Figure 7:
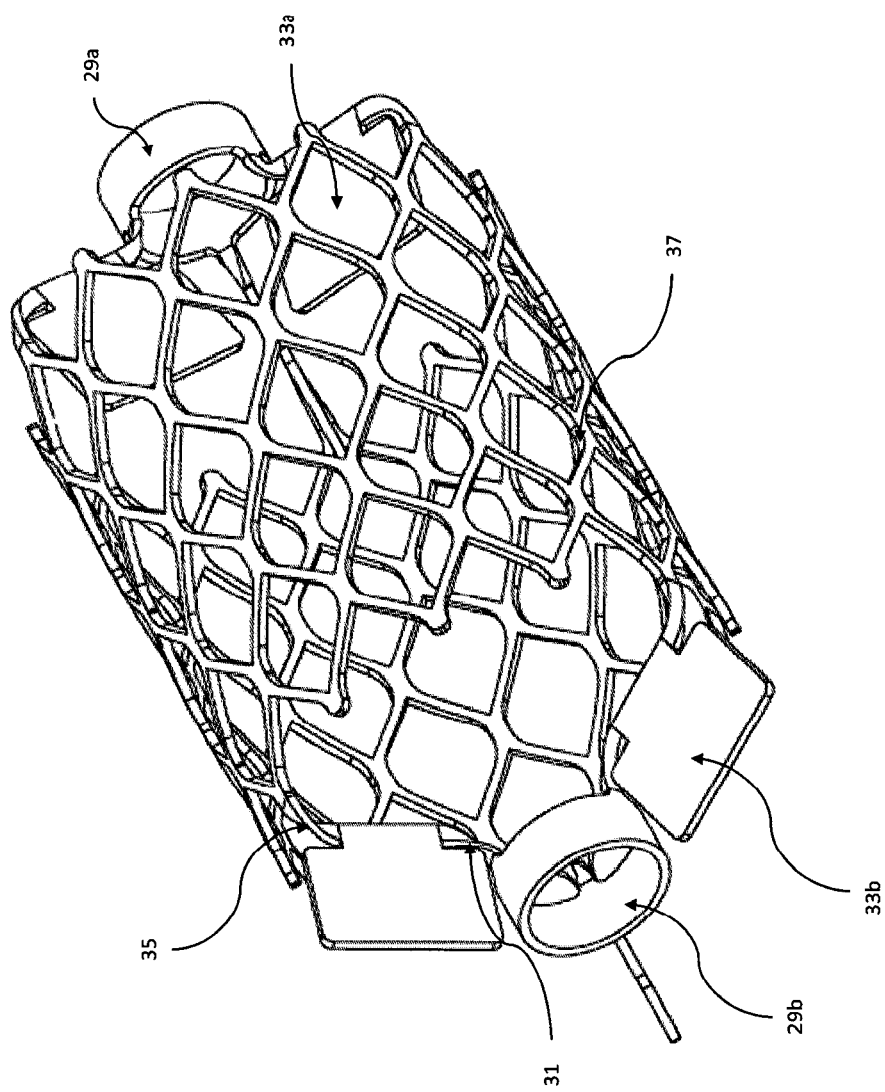
FIG. 7 embodies the expanded inner main stent body which substantially has the inward folded proximal vane elements and outward folded distal vane elements movably coupled to the expanded proximal vane struts and distal vane struts.

FIG. 7 embodies the expanded inner main stent body which substantially has the inward folded proximal vane elements 33a and outward folded distal vane elements 33b movably coupled to the expanded proximal vane struts 31 and distal vane struts 35. The inward folding vane elements 33a assist in directing the inflow of fluid as well as assisting the augmentation of impeller flow. The outward folding distal vane elements 33b assist in straightening the flow of fluid as well as augmenting the pressure head of the impeller rotation.

Figure 8:
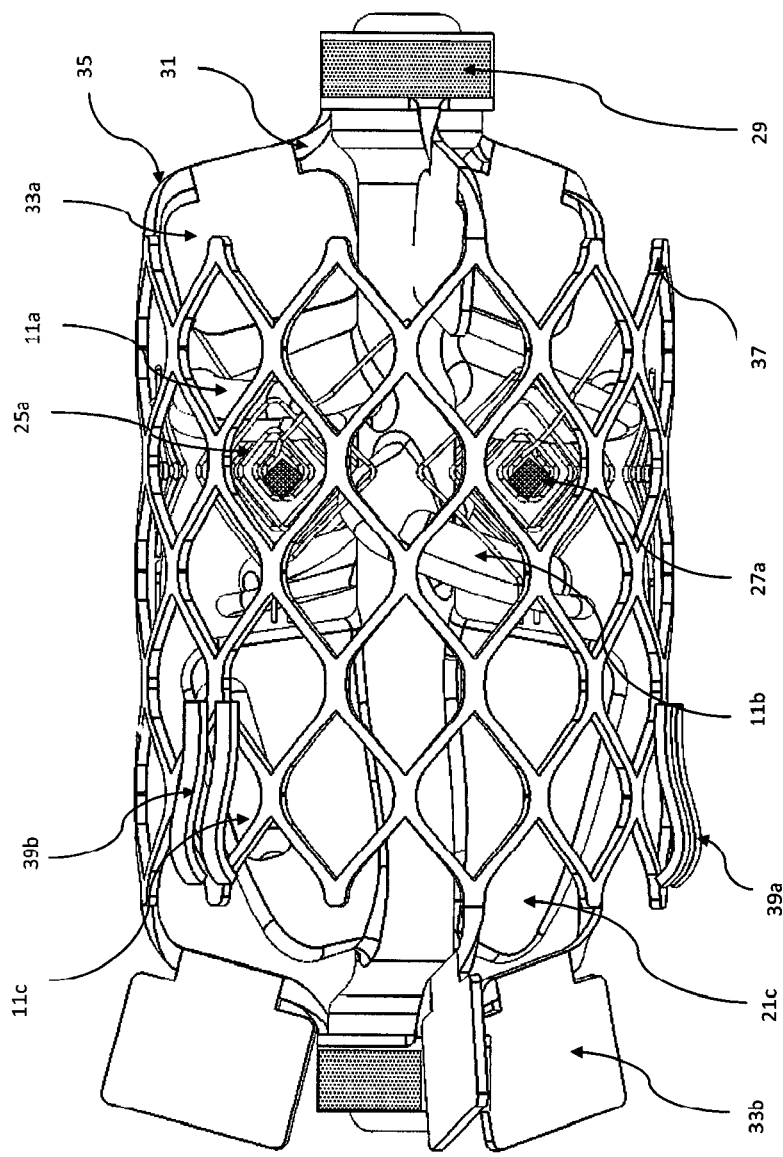
FIG. 8 illustrates an embodiment of an expandable motor that substantially incorporates the expandable impeller pump with magnets on blade edges.

FIG. 8 is an embodiment of an expandable motor that substantially incorporates the expandable impeller pump with magnets on blade edges illustrated in 11a, 11b and 11c. The expandable motor is further defined by the stator coil row 25a with the integrated ferromagnetic elements 27a supported on the inner stent main body 37. The application of an alternating electromagnetic current within the stator coil 25a creates a magnetic flux interaction with the embedded blade magnets 11a, 11b and 11c with a resultant an electromagnetic torque force. The expanded impeller blade 5 of the third row embodies the plurality of blades that rotate about the central support elements 29 as the electromagnetic torque force translates to rotation about the central axis. The inner main stent 37 is movably coupled to the inward folding vane element 33a by the proximal vane strut 31 and distal vane strut 35 which expands to a preset formation on expansion, similarly, the outward folding vane element 33b expands to a predetermined angulation that straightens and redirects the fluid exiting the pump so as to maximize the pressure augmentation while minimizing blood trauma and shear. Notably, the inner stent main body 37 has position slots as illustrated by 39a and 39b that assist in positioning and locking the inner main stent to an outer nested stent.

Figure 9:
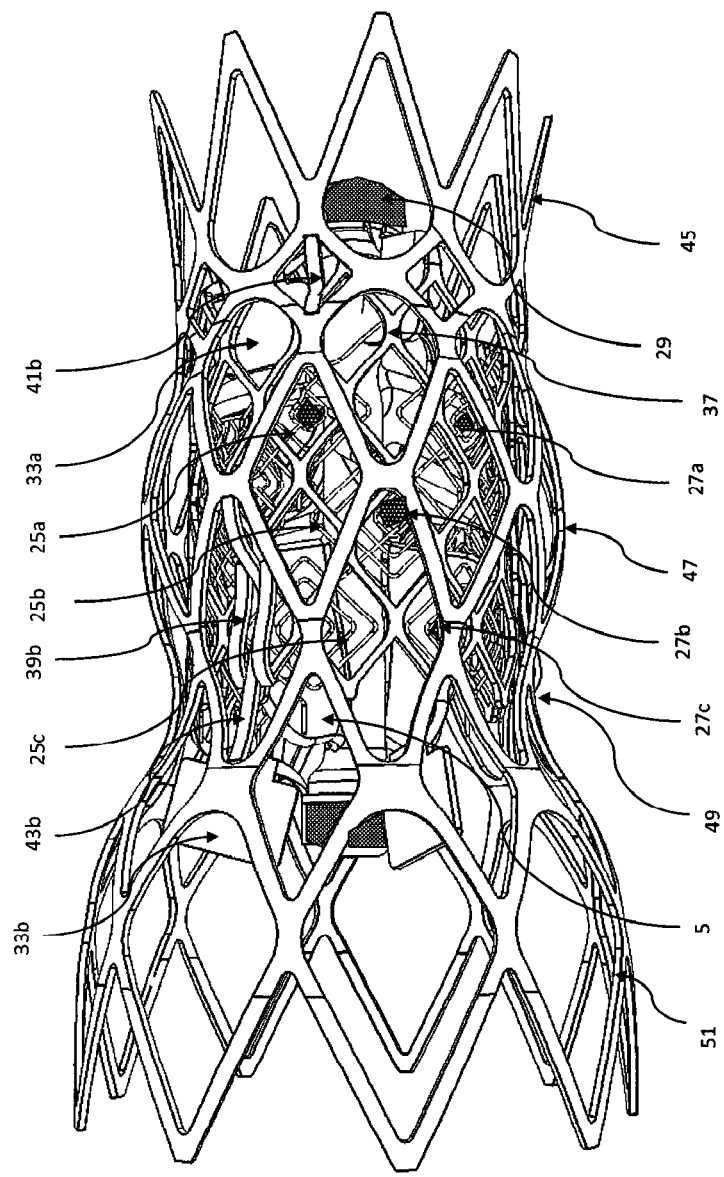
FIG. 9 illustrates an embodiment of the nested stent and the inner main stent.

FIG. 9 is an embodiment of the nested stent and the inner main stent. The nested stent is substantially described by a proximal annular flare 45, a sinus expansion 47, sino-tubular contact support 49 and a distal aortic flare 51. The interlocking of the two stent systems is embodied in the interaction of the paired distal position slots 39b of the inner main stent with the distal position strut of the nested stent 43b and further exemplified by the proximal position struts 41b of the nested stent. The paired distal position slots 39b are movably coupled to the single position strut 43b which allows for the extraction and reimplantation of the inner expandable motor and impeller pump by constraining the inner main stent 37, vanes 33a and 33b, impeller 5, the motor coil elements 25a, 25b and 25c and motor ferromagnetic elements 27a, 27b and 27c.

Figure 10:
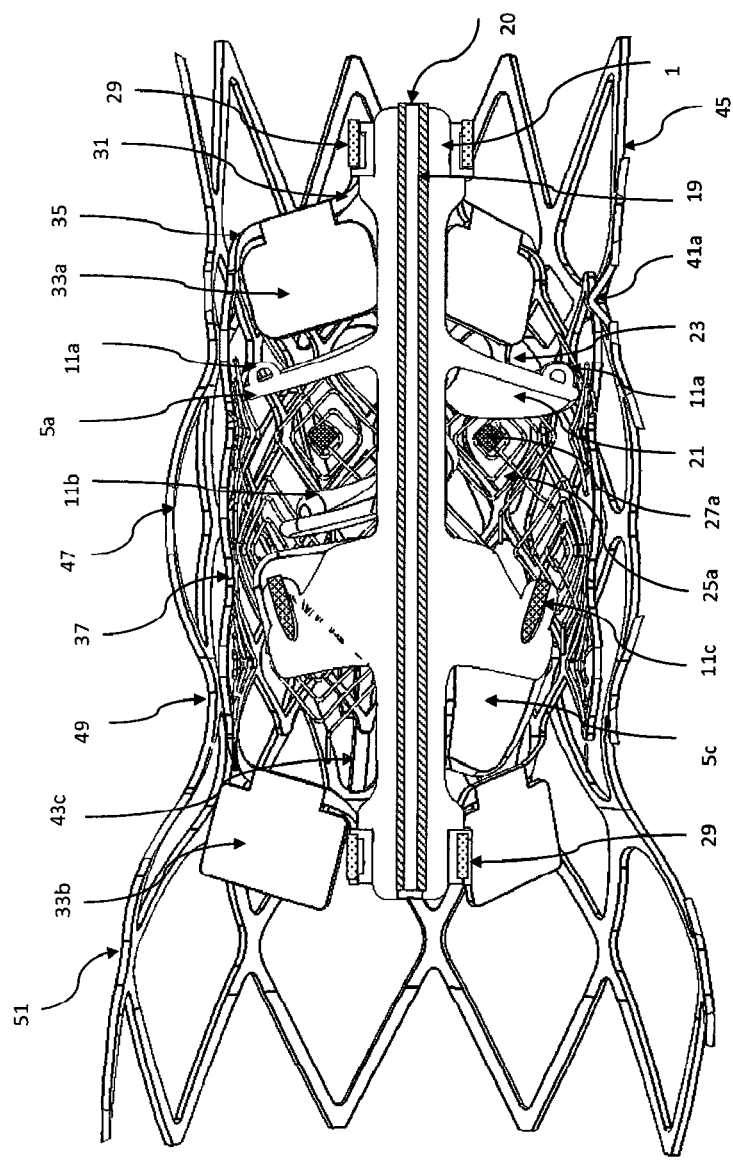
FIG. 10 illustrates a cross-section of the nested outer stent components, inner main stent, expanded motor and expanded impeller.

FIG. 10 is a cross-section of the nested outer stent components 45, 47, 49, 51, inner main stent 37, expanded motor 25a, 27a and expanded impeller 5a and 5c. The impeller blades edged with the embedded magnets 11a, 11b and 11c are movably coupled around the central rotating element 17. A central rotating element support shaft 19 is hollowed out to facilitate the passage of a guidewire 20 which in turns allows for accurate positioning and deployment within the arterial tree or venous system. The impeller blades 5a and 5c represent a plurality of blades that are clocked and interleaved, each with a suction face 21 and a pressure face 23 that are configured upon the operational expansion of the constrained system. The cylindrical support elements 29 are movably coupled with the bearing system 1 at each end of the central rotating element 17. The interlocking and stabilization of the inner stent 37 and the nested outer stent interaction is embodied in the proximal position strut 41a of the outer nested stent and the single distal position strut 43c of the nested stent.

Figure 11:
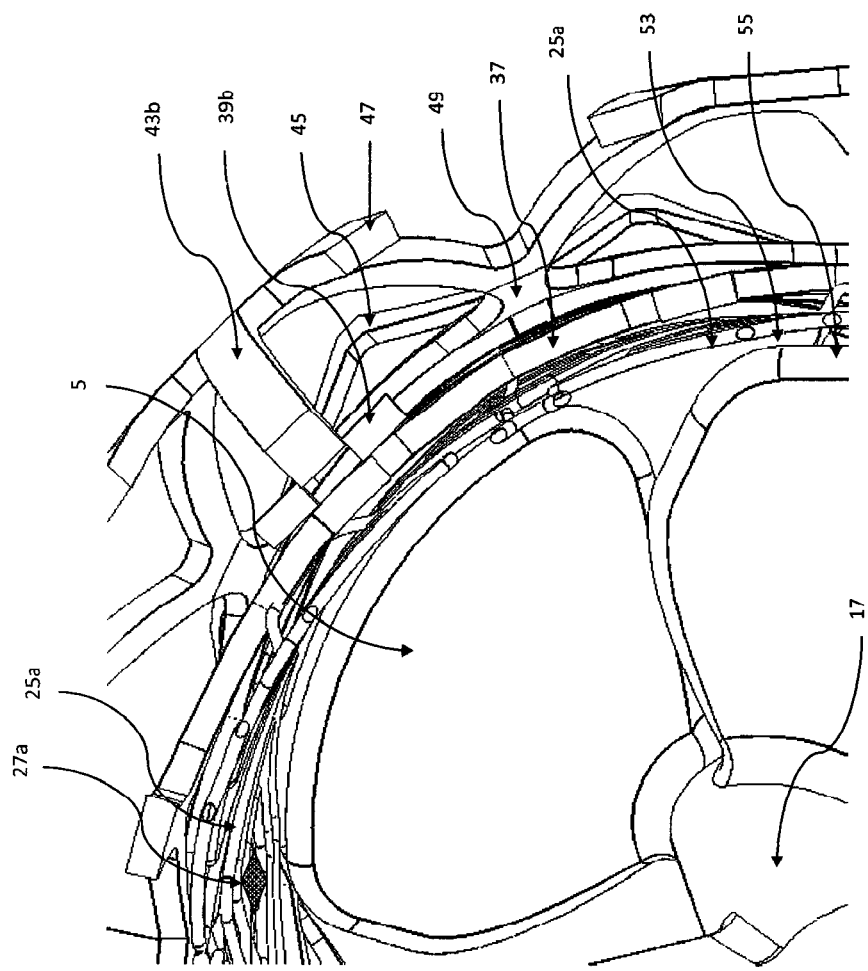
FIG. 11 illustrates a magnified cross-section of the impeller blade, stator coils, inner stent and nested inner stent.

FIG. 11 is a magnified cross-section of the impeller blade 5, stator coils 25a, inner stent 37 and nested inner stent 45, 47 and 49. The proximity of the impeller blade edge 55 to the stator coils 25a allows for the electromagnetic flux lines to be formed across the air gap 53 between the embedded ferromagnetic elements 27a, stator coils 25a and blade magnets. The cross-section also demonstrates the interlocking of the paired distal position slots of the inner stent 39b and the distal position strut of the nested outer stent 43b which stabilizes for axial and radial displacement. In one embodiment, the elastic deformation of the distal position strut with axial force could result in the displacement of the inner stent thus allowing for its removal and interchange should the unit become dysfunctional, In another embodiment, the inner main stent could be equipped with a tri-leaflet valve, such that if there is recovery of the heart after a period of support from the ventricular assist device, then normal valvular function can reestablished. The interchange of the pump unit for a valve unit can be performed by current percutaneous aortic valve replacement techniques.

Figure 12:
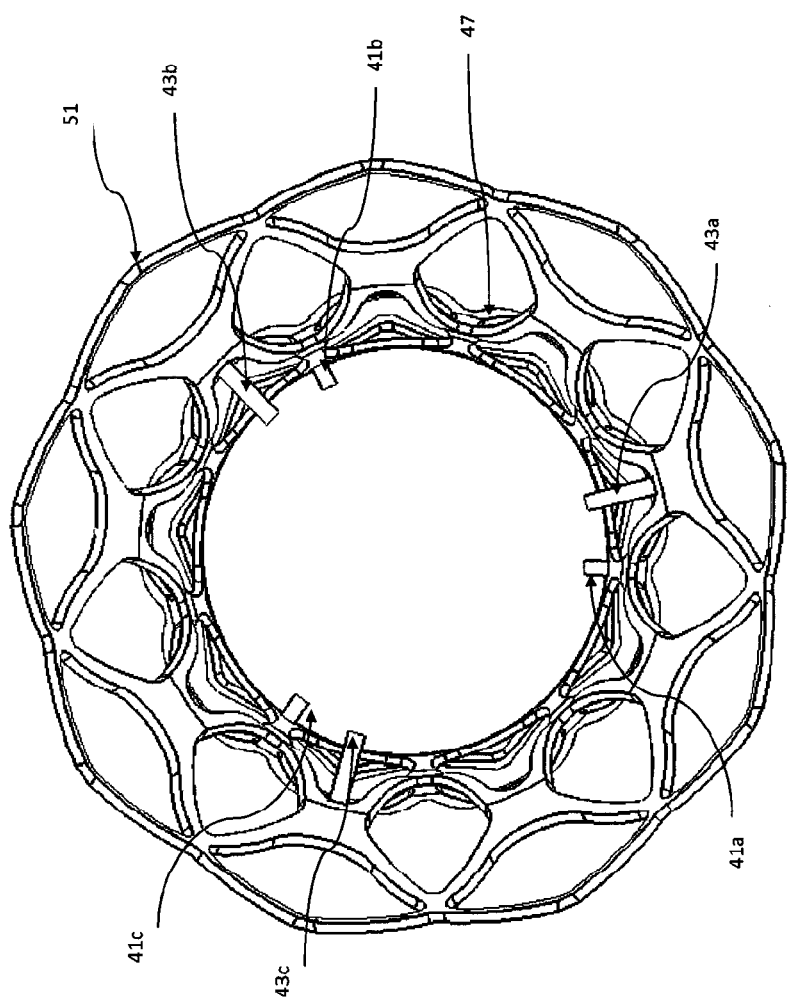
FIG. 12 illustrates the cross-sectional view of the nested outer stent proximal and distal ends.

FIG. 12 Illustrates the cross-sectional view of the nested outer stent proximal and distal ends. The distal aortic flare 51 is seen with the distal position struts 43a, 43b and 43c. The proximal position struts 41a, 41b and 41c are clocked at an offset to the distal position struts, The two strut system provide restraint against the rotational and radial forces of the impeller of the inner main stent. The two strut systems also provide restraint against the radial compressive and expansive forces of the aortic annular and sino-tubular motion during the systolic and diastolic phases of the cardiac cycle.

Figure 13:
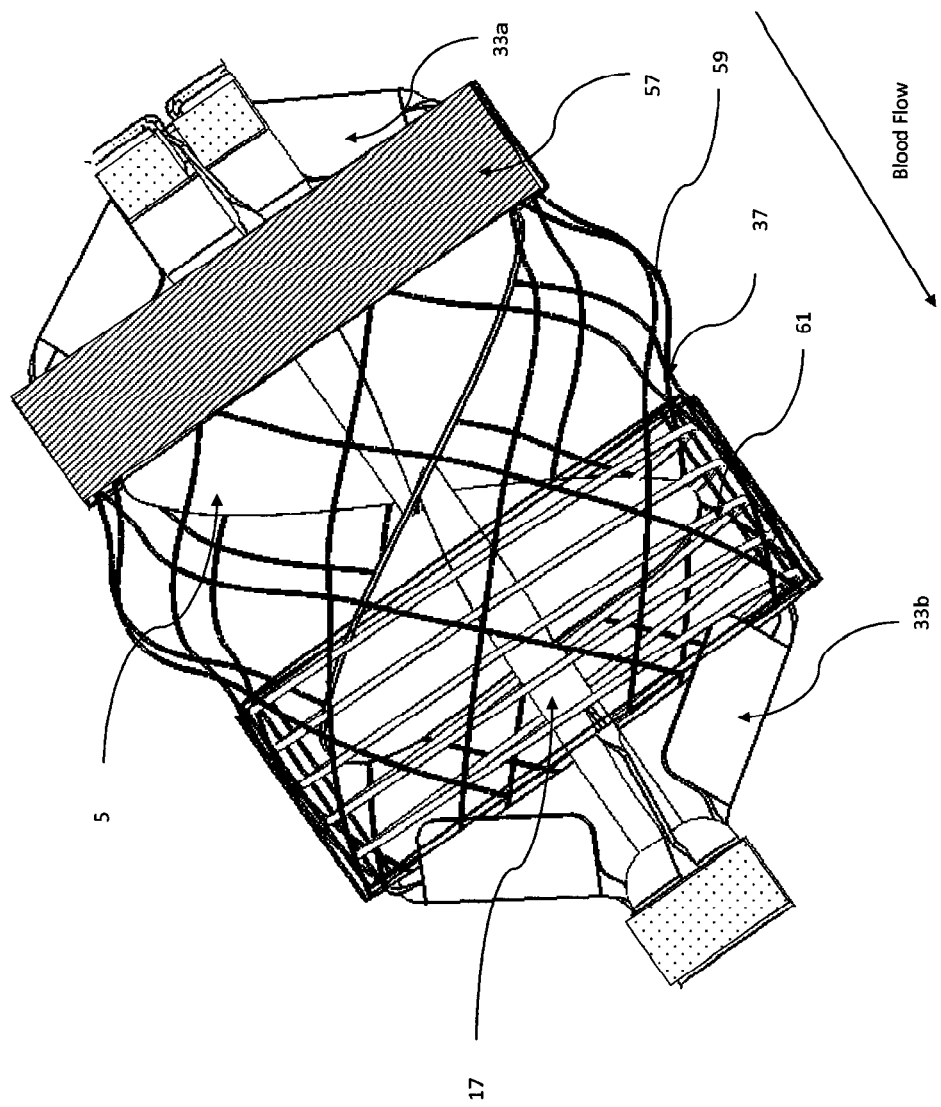
FIG. 13 illustrates that reinforcement of the inner main stent body radial diameter can also be provided by shroud elements stationed at various positions along the length of the inner stent.

FIG. 13 Reinforcement of the inner main stent body radial diameter can also be provided by shroud elements 57 stationed at various positions along the length of the inner stent. Energy transfer coils 61 can also be patterned within medical textiles to collapse with constraint of the system and expand on deployment or on activation and these also serve as additional reinforcement mechanisms. In another embodiment of the inner stent body expands circumferentially 59 at various points along its length to different radial dimensions to allow for better seating of the stent within the aortic wall and more specifically into the coronary sinus of the aortic valve and outflow tract. These areas of circumferential expansion 59 along with the shrouding elements 57 and the energy transfer elements 61 create augmented flow patterns to both the systemic and coronary system if the unit is deployed so as a replacement for the native aortic valve. The most optimal deployment strategy may vary with the native heart function however, the impeller pump blades 5 rotating about the central element 17 when deployed at the aortic root does serve to replace the native aortic valve, while being in line with the flow of blood, thus augmenting systolic flow and limiting diastolic regurgitation. Additional flow straightening and diffusing is supplied by the proximal vane elements 33a and distal vane elements 33b.

Figure 14:
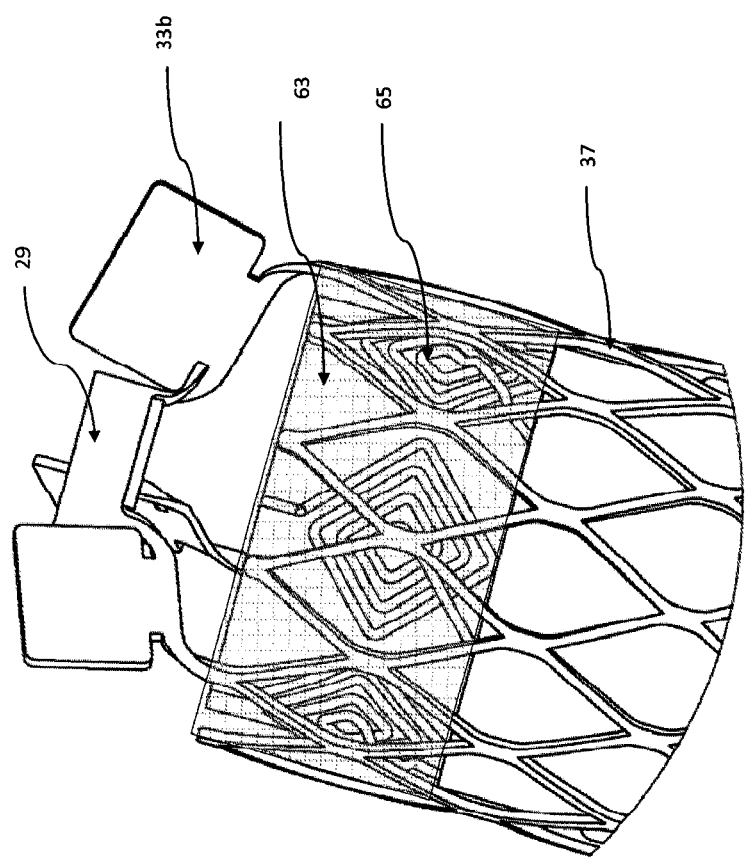

FIG. 14 Illustrates a woven medical textile fabric 63 with insulated wire coils 65 woven in. The inner stent main body 37, distal vane elements 33b and cylindrical support element 29 are also illustrated. The integration of a motor design onto a stent that is compressible requires flexible elements. Motor design requires the integration of magnetic and electromagnetic elements. The placement of electromagnetic elements onto a stent requires a platform upon which stator coils are configured. In one embodiment the stator coil base material is a woven fabric 63 such as polyester or polyethylene. Finely woven medical textiles are compressible and of low profile and can allow the attachment of insulated wire coils 65 in patterns that produce magnetic lines of flux. The integration of woven medical fabrics onto the stent main body network of wires 37 can be onto the inner or outer aspect or, as an integral component of the stent design such that the fabric and wire network are interwoven. In another embodiment the attachment of the fabric can be with permanent material wound in a spiral pattern or individual attachment windings or knots. In another embodiment the winding of electromagnetic coils can be without a fabric backing and as an interwoven coil that expands along with the expansion of the stent into a prearranged configuration and pattern that allows for magnetic field alignment. In another embodiment the woven fabric can be placed in a pattern to match the pattern of magnets within the impeller pump blades for example, to configure the compressible motor as a brushless DC motor. In another embodiment, the pattern of the stator coils and medical textile configures to a circular iris of an even number of stator coils that are circumferentially arranged and typically overlap when in the compressed state. This embodiment of stator coils woven into a medical textile can be patterned to follow the magnetic flux lines created by the magnetic material within the impeller blades.

Figure 15:
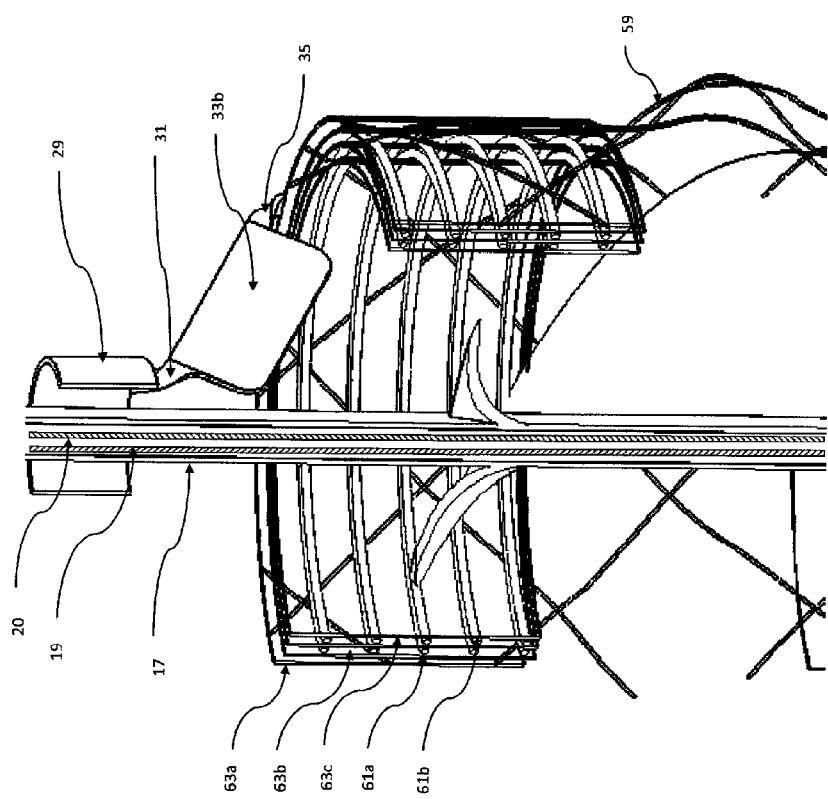
FIG. 15 illustrates a cross-sectional image of the inner stent and the energy transfer coil.

FIG. 15 Illustrates a cross-sectional image of the inner stent and the energy transfer coil. The relative position of the energy transfer coils 61a and 61b to inner stent components illustrated. The area of circumferential expansion 59, the cylindrical support element 29, central rotating element 17, central rotating element support shaft 19, hollow guidewire passage 20, proximal vane strut and distal vane struts 35 are shown. The energy transfer coils is demonstrated in one embodiment as two layers of wire coils 61a and 61b in a compressible configuration, insulated with a medical textile 63a and 63b. The medical textile can be interwoven within the wire frame or layered on the outer or inner surface.

Figure 16:
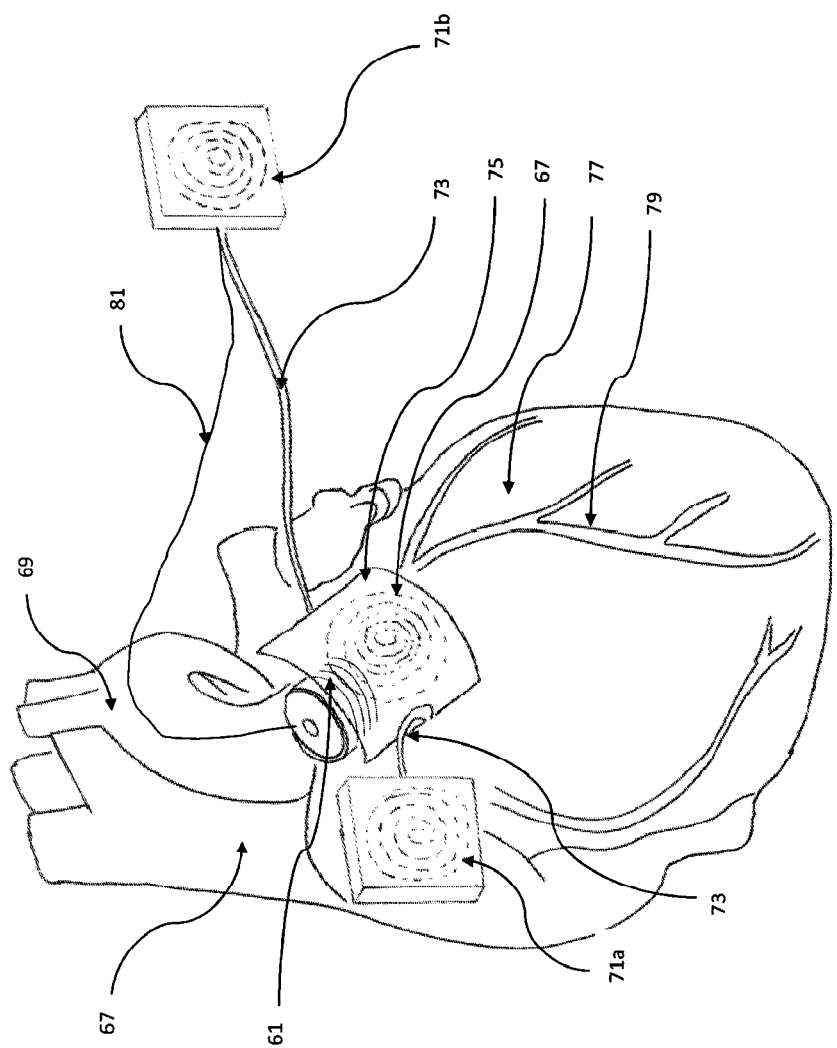
FIG. 16 illustrates a powering scheme that utilizes wireless energy transfer.

FIG. 16 Illustrates a powering scheme that utilizes wireless energy transfer. The powering of the electromagnetic coils requires an external power source. Recent advances in wireless telemetry within the human body have made it possible to consider continuously powering of a collapsible pump. FIG. 16 illustrates power coils 67 that are described on the outside of the aorta 69 that is connected to a battery source 71a and 71b by a coaxial cable 73. In one embodiment the power coils 67 are an integrated onto a polygonal shape of flexible or semi-rigid material 75. This is positioned on the outside of the aorta 69 in the ascending or descending portion or on the surface of the heart 77, taking care to avoid the epicardial arteries 79. The placement of this wireless power coil 67 on the outer aspect of the ascending aorta allows for wireless energy transmission to an inner stent coil 61 located at the level of the ascending aorta and aortic root. In one embodiment, the energy coil outside of the aorta 67 is a coil in a polygonal shape preferably rectangular or square with several loops that are insulated wires, typically copper or of another conductive material. These loops are formed on a mandrel and sewn onto a medical fabric which is in turn attached to a delivery system. In one embodiment the coils and fabric are compressed into a tubular fashion and introduced by a port into the pleural cavity and delivered by minimally invasive means to the outer aortic wall. A certain maximum and minimum distance can be achieved based on the anatomical factors which reflect the patients past medical and surgical history. These loops can be delivered prior to the implantation of the stent carrying the pick-up coils for the energy transmission. The size and orientation of the transmission coil patch is matched to the size and orientation of the pick-up coils on the inner stent 61 so that the magnetic fields align to optimize energy transmission efficiency. In another embodiment the coils are layered on an insulating material or medical textile 63*a* and 63*b* and are constructed of overlapping and connected wires. An alternative embodiment describes a direct energy cable 81 to power the expandable motor and pump that traverses the aortic wall or runs the length of the aorta and exits via a peripheral vessel.

Figure 17:
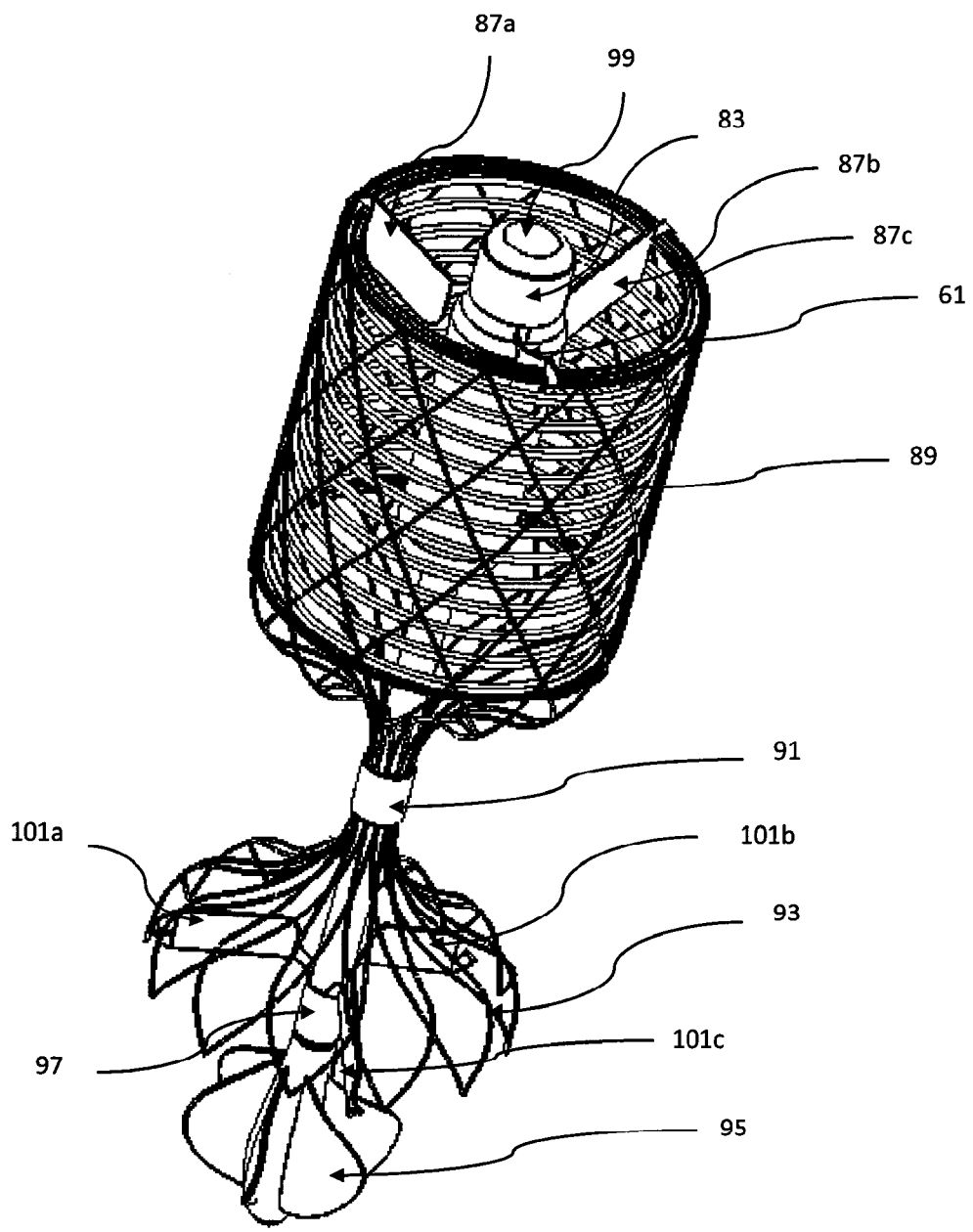
FIG. 17 illustrates a transvalve stent impeller design that allows for preservation of the aortic valve.

FIG. 17 Illustrates a transvalve stent impeller design that allows for preservation of the aortic valve. The system is designed around a collapsible stent main body that is described as a network of wires 89 with integrated energy coils 61. The central shaft 99 supports a cylindrical support element 83 that is movably coupled to a plurality of distal vane elements 87*a*, 87*b* and 87*c*. The ability to traverse the aortic valve and maintain the function of the pump is derived by constraining the network of wires 89 for passage through the valve orifice. Once the proximal and distal components are expanded, the constraining element 91 at the level of the valve allow for closure of the native valve and maintenance of its function. A proximal subannular expansion of the wire network forms an annular shroud 93 which is again supported by a plurality of proximal vane elements 101*a*, 101*b* and 101*c*. The expandable impeller 95 is supported by the proximal cylindrical support 97.

Figure 18:
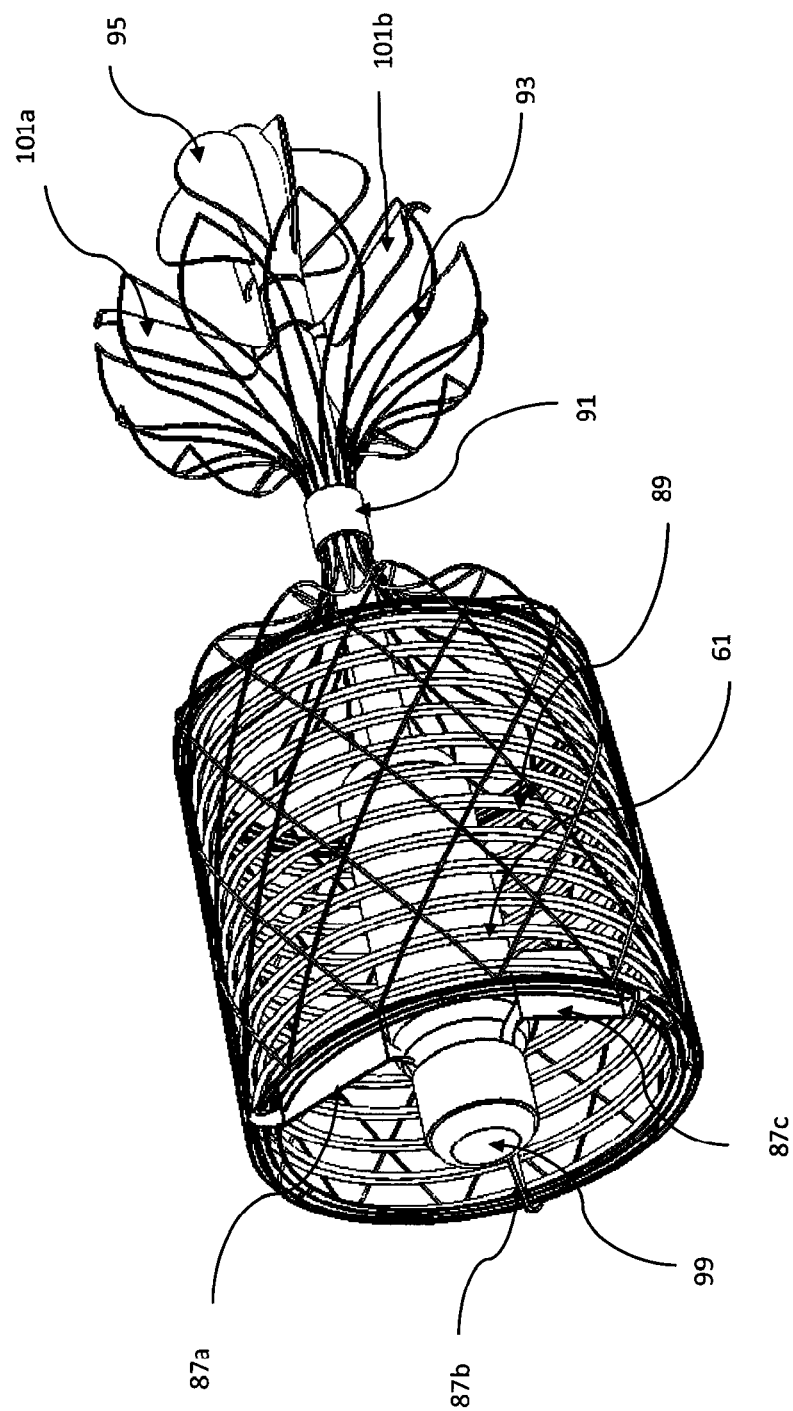
FIG. 18 illustrates an oblique view of the transvalve stent impeller.

FIG. 18 illustrates an oblique view of the transvalve stent impeller. The embodiment described has a network of wire elements 89 that are initially constrained for passage across the cardiac valve then expanded. The proximal component forms an annular shroud 93 that surrounds the collapsible impeller 95. The distal component forms a wire network that is cylindrical and conforms to the ascending aorta. The wire network may embody a plurality of integrated energy coils 61 for energy transfer and support as well as independently functioning as stator coils for an expandable motor. The distal support elements include a plurality of distal vane elements 87*a*, 87*b*, and 87*c* that are movably coupled to a central shaft 99.

Figure 19A:
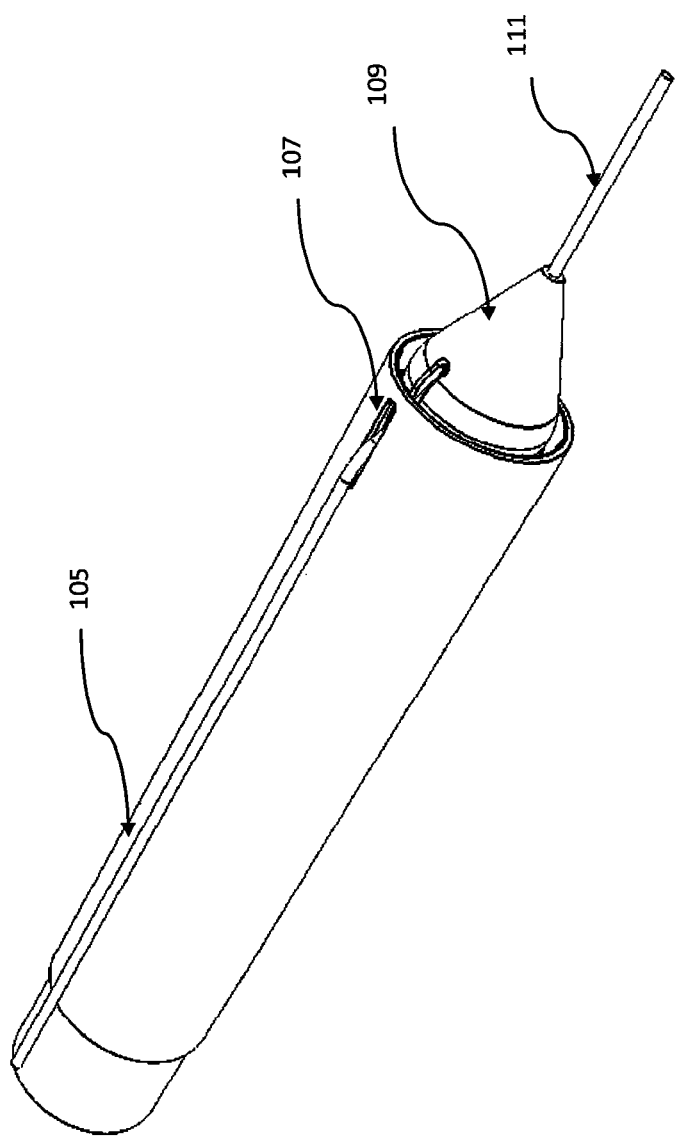
FIG. 19a illustrates a monorail delivery system that is constrained.

FIG. 19*a* Illustrates a monorail delivery system that is constrained. The guidewire 111 is alongside the outer catheter sheath 105 and passes through a small slot 107 at the tip of the catheter sheath. The wire extends through the protective tip sheath 109 to exit at the center-point of the delivery system.

Figure 19B:
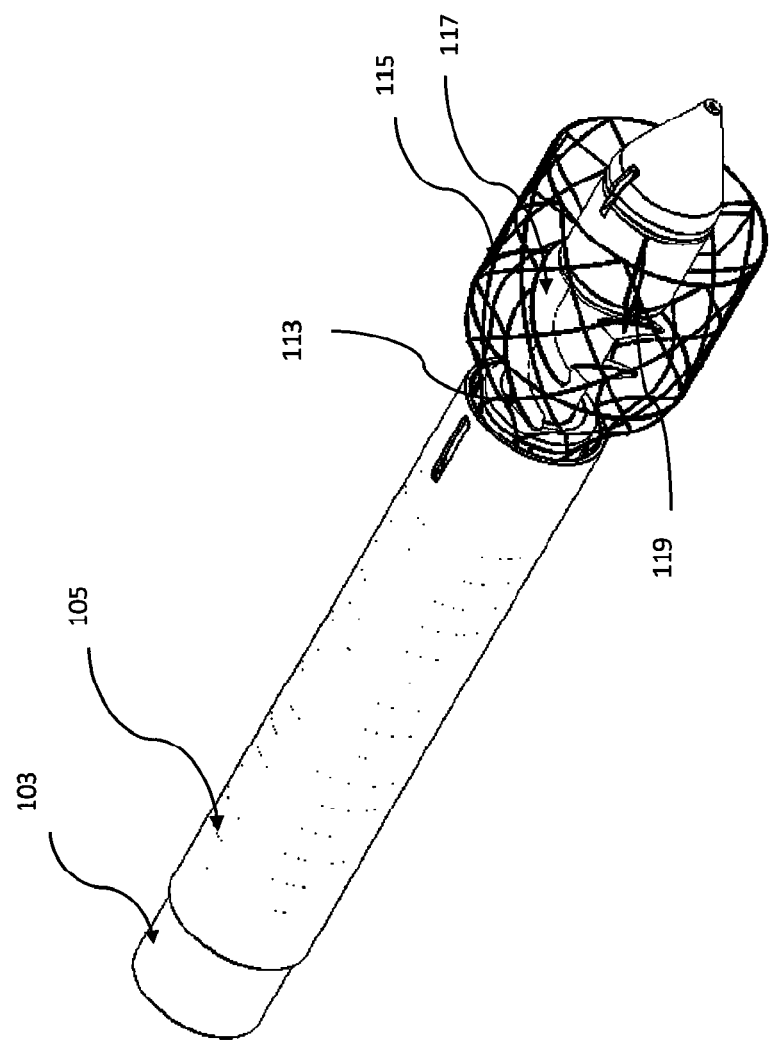
FIG. 19b illustrates the expansion of the stent from the restraining outer sheath.

FIG. 19*b* Illustrates the expansion of the stent from the restraining outer sheath 105. An inner sheath 103 is used to apply axial force to the distal portion of the restrained stent. The stent on expansion 115 has a constrained area 113 that remains within the sheath until final positioning is confirmed. The impeller 117 shown is unexpanded. The proximal vane 119 is expanded and provides initial support for the expanded proximal portion of the stent.

While the foregoing details what is felt to be the preferred embodiment of the invention, no material limitations to the scope of the claimed invention are intended. Further, features and design alternatives that would be obvious to one of ordinary skill in the art are considered to be incorporated herein.

The scope of the invention is set forth and particularly described in the claims hereinbelow.

I claim:

1. A cardiac augmentation pump having a compressible construction which allows for a minimally invasive pump implantation and augmentation of cardiac flow, comprising:
    a cylindrical-shaped support that is operatively capable of suspending a motor within the vascular system while also supporting an impeller pump that can be made to be collapsible;
    a main stent body which is operatively capable of expanding during said minimally invasive pump implantation;
    an impeller pump support coupled to said main stent body through a plurality of struts and vanes;
    an expandable woven medical textile fabric supporting an expandable wire network defining electromagnetic elements placed onto said main stent body and operably capable of expanding with said main stent body using said minimally invasive pump implantation into a pre-arranged configuration;
    a fluid impeller having impeller blades;
    a central rotating element supported by said impeller pump support on which the impeller blades are movably coupled; and
    electromagnetic elements coupled with said central rotating element and capable of operably interacting with said expandable wire network when expanded into said pre-arranged configuration to thereby define a motor; and
    wherein said cylindrical-shaped support further comprises a superstructure with said motor integrated therein and which is self-expanding and will restore to a predictable configuration while allowing for full expansion of said impeller suspended within.

2. The cardiac augmentation pump of claim 1, wherein said cylindrical-shaped support further comprises cylindrical-shaped support elements attached and movably coupled to a central stent by struts that are fashioned by laser cutting one single tube of material, said material having the property of being compressible and expandable restoring to the original dimensions with sufficient radial and axial force to withstand the surrounding compressive forces of the cardiac environment.

3. The cardiac augmentation pump of claim 1, wherein said struts orient on expansion of said pump to assist in directing the flow of fluid or blood, at the proximal portion of said pump directing fluid by said vanes to straighten flow, and at the distal portion of said pump exiting fluid is directed by said vanes to diffuse accelerated rotating fluid, said vane elements each having different orientation based on a position within said stent structure.

4. The cardiac augmentation pump of claim 1, wherein said strut and vane elements are compressed to allow for delivery by minimally invasive means.

5. The cardiac augmentation pump of claim 1, wherein said main stent body further comprises portions being of a rigid, predictable diameter which allows for a closer gap distance between elements of said motor, thus improving motor efficiency.

6. The cardiac augmentation pump of claim 1, wherein said electromagnetic elements coupled with said central rotating element further comprise magnetic material coupled with said impeller blades and adapted to be operatively aligned with a magnetic field created by said expandable wire network during operation.

7. In combination, a wireless power source and a cardiac augmentation pump having a compressible construction and structured around a cylindrical-shaped support that suspends a motor within the vascular system while also supporting an impeller pump that can be made to be collapsible, the pump which allows for a minimally invasive pump implantation and augmentation of cardiac flow, said wireless power source comprising:

a source of electrical energy;

a first wireless energy coil adapted for operative placement external to an aorta and powered by said source of electrical energy; and a second wireless energy coil adapted for operative placement within an aorta and directly electrically coupled to said cardiac augmentation pump and capable of receiving electrical energy from said first wireless energy coil to thereby power said cardiac augmentation pump.

8. A trans-valve cardiac augmentation pump that allows for preservation of the aortic valve, comprising:

a collapsible stent main body having a network of wires that are adapted to operatively traverse the aortic valve;

a collapsible impeller pump supported within said collapsible stent main body;

a motor supported by said collapsible stent main body operative to drive said collapsible impeller pump;

a proximal subannular expansion of said wire network define an annular shroud that surrounds said collapsible impeller pump;

a distal expansion of said wire network adapted to operatively expand to a generally cylindrical geometry and conform to an ascending aorta;

wherein said network of wires is adapted to operatively pass through an aortic valve orifice and allow for closure and maintenance of function of a native aortic valve.

\* \* \* \* \*